United States Patent [19]

Buchan

[11] Patent Number: 4,516,571

[45] Date of Patent: May 14, 1985

[54] MEDICAL DEVICE, ITS PREPARATION AND USE

[75] Inventor: Ian A. Buchan, Stansted Mountfitchet, England

[73] Assignee: Smith and Nephew Associated Companies p.l.c., England

[21] Appl. No.: 587,470

[22] Filed: Mar. 8, 1984

[30] Foreign Application Priority Data

Mar. 10, 1983 [GB] United Kingdom ............... 8306663
Nov. 9, 1983 [GB] United Kingdom ............... 8329877

[51] Int. Cl.³ ............................................. A61F 13/00
[52] U.S. Cl. .................................. 128/132 R; 128/156
[58] Field of Search ............... 128/149, 153, 155, 156, 128/165, 166, 169, 132 R; 604/368

[56] References Cited

U.S. PATENT DOCUMENTS 3,486,968 12/1969 Mater ................................. 428/246
3,548,420 12/1970 Spence ..................................... 3/20
3,858,379 1/1975 Graves ..................................... 53/25
4,456,642 6/1984 Burgdorfer et al. ................. 428/68

FOREIGN PATENT DOCUMENTS 0057838 1/1982 European Pat. Off. .

Primary Examiner—John D. Yasko
Assistant Examiner—Christa K. Scott
Attorney, Agent, or Firm—Jacobs & Jacobs

[57] ABSTRACT

A device suitable for the prophylaxis of pressure sores which device comprises a gel retained within a flexible elastomeric envelope which envelope has a body contacting surface which is a film having a moisture vapor transmission rate of greater than 300 g/m²/24 hr⁻¹ at 37° C. at 100% to 10% relative humidity difference characterized in that the device is 5 to 25 mm thick and may be worn on the body and the gel is a mobile moisture absorbing hydrophilic gel is described.

14 Claims, 5 Drawing Figures

MEDICAL DEVICE, ITS PREPARATION AND USE

The present invention relates to devices for application to the pressure bearing surfaces of humans, for example bedridden patients, for the prophylaxis of pressure sores. In particular it relates to devices which are particularly suitable for application to those areas of the patient such as the heel and sacrum which are most at risk of developing pressure sores which device comprises a hydrophilic mobile gel retained within a flexible, elastomeric envelope. Also described are methods of forming such devices and to their use as pads which maybe applied to the body of the patient for the prophylaxis of pressure sores.

A prophylactic device consisting of a cross-linked water insoluble immobile polyurethane gel contained within an outer envelope has been described in European Patent Specification No. 0,057,838. The prophylactic device described in European Patent Specification No. 0,057,838 is adapted to be used as a cushion or a mattress and as such is only providing protection to the patient when the patient is actually in position on the prophylactic device. If the patient is moved from his bed or chair, where he is on the prophylactic device for example to another bed, a chair, then he will no longer be afforded protection. Also it is found that a mobile gel filled device is more effective than the cross-linked immobile gel filled device at reducing the pressures experienced by a patient when lying on one of these devices and has greater conformability.

Accordingly the present invention provides a device suitable for the prophylaxis of pressure sores which device comprise a gel retained within a flexible elastomeric envelope which envelope has a body contacting surface which is a film having a moisture vapour transmission rate of greater than 300 g/m$^2$/24 hr$^{-1}$ at 37° C. at 100% −10% relative humidity difference characterised in that the device is 5.0 to 25 mm thick and may be worn on the body and the gel is a mobile moisture absorbing hydrophilic gel.

Suitable examples for the film which contacts the body of the wearer of the device are backing materials described in British Patent Specification No. 1280631 which is incorporated herein by cross reference.

Apt polymers for forming the film are polyurethanes such as those known as Estane (Registered Trade Mark). Suitable Estanes include Estane 5702, 5701, 5714F and 58201. Other preferred polymers for forming the film are polyetherester block copolymers such as Hytrel (Registered Trade Mark). Suitable Hytrels include Hytrel 4056. Yet other preferred polymers for forming the film are polyether polyamide copolymers such as Pebax (Registered Trade Mark). Suitable Pebax include Pebax 2533 SN 00.

The thickness of the film employed in the device of this invention is chosen to produce the desired moisture vapour transmission rate (MVTR). Suitably the thickness of the film which will give the correct MVTR and be sufficiently strong to withstand the pressure applied to it will be in the range 25 to 100 microns. The film will be chosen so that its MVTR will be greater than 300 g/m$^2$/24 hr$^{-1}$ and preferably will be greater than 500 g/m$^2$ 24 hr$^{-1}$, at 37° C. and at 100% −10% relative humidity.

For ease of manufacture it is convenient to form the envelope entirely of a moisture vapour permeable film. However, it is envisaged that the hydrophilic gel may be retained between a film which is to contact the skin of the wearer which has the MVTR set out in the preceeding paragraph and a film having a lower MVTR (for example one which for practical purposes is a moisture vapour impermeable film). The moisture vapour impermeable film may be a polyolefin, polyvinylchloride or the like.

In a favoured aspect of the invention the surface of the device which is to contact the skin may carry an adhesive layer whereby the device may be adhered to the skin in use. By adhering the device to the skin it is less likely to be dislodged or moved out of place if the wearer moves or is moved. Suitable adhesives must be compatible with the skin, thus they will normally be hypoallergenic. Favourably the adhesives will be synthetic polymers or mixtures thereof. Such adhesives may be selected from those described in British Patent Specification No. 1280631 and European Patent Application No. 35399, both of which are incorporated herein by cross-reference. Preferred adhesives are those which have an MVTR such that the adhesive together with the film which is in contact with the skin has an MVTR of greater than 300 gm$^{-2}$ 24 hr$^{-1}$ and more preferably greater than 500 gm$^{-2}$ 24 hr$^{-1}$ when measured at 37° C. and 100% −10% relative humidity. Suitable adhesives include those formed from polyacrylates or polyvinyl ethers.

Normally the adhesive will be applied to the film in the form of a continuous layer. However it is envisaged that the adhesive could be applied to form a discontinuous layer such as a pattern spread layer. If desired the adhesive may incorporate an antibacterial agent such as a chlorhexidine salt.

In another aspect the film which forms the envelope (and preferably the body contacting layer of the envelope) may be extended to form a margin or flange around the gel filled envelope. The body contacting layer will preferably carry an adhesive layer for adhering the device to the skin. This layer may be present over the whole of the device's surface or only on the margin. The adhesive layer may be a continuous layer or a discontinuous layer such as a pattern spread layer.

It is generally less preferable that the non-body contacting film may extend beyond the envelope and be coated on the side which may be brought into contact with the body with a suitable adhesive.

In a less preferred aspect of the invention there is no margin or flange and the surface of the device which is to contact the skin may carry an adhesive layer whereby the device may be adhered to the skin in use.

It is envisaged that once applied to the body the device can remain in position for a week or even longer. During this period the moisture produced by normal perspiration of the skin under the device must be removed otherwise the skin will become waterlogged and degenerate. It has now been found that this can be achieved if the moisture is transmitted through the wall of the envelope and absorbed by the gel. The gel in the envelope is therefore selected to be hydrophilic and absorb the moisture generated by the skin during the wearing period. The gel is suitably introduced into the envelope in an anhydrous state so that the gel is chosen to be jelly-like and mobile even when anhydrous. Suitable hydrophilic mobile gels include polyurethanes, polyethylene glycols, and polyoxyethylene-polyoxypropylene diol block copolymer gels which have the correct viscosity characteristics and are capable of flowing in a manner which distributes an applied pressure approximately evenly over their surface. Apt mobile hydrophilic gels are hydrophilic polyurethanes described in, for example International Application No. WO 82/01306, which is incorporated herein by cross-reference. Preferred hydrophilic mobile gels are linear polyether polyurethanes formed from random polyoxyethylene-polyoxypropylene diol copolymers and a di-isocyanate. Preferred random polyoxyethylene-polyoxypropylene diol copolymers include Breox 75W-270 (Registered trade mark).

The preferred linear polyether polyurethanes are made by mixing the appropriate volume of random polyoxyethylene-polyoxypropylene diol copolymer, di-isocyanate such as Desmodur W (Registered Trade Mark) and an antioxidant such as Irganox 1010 (Registered Trade Mark) together and heating to a temperature of between 40° C. and 90° C. and preferably between 60° C. and 70° C. and then adding a catalyst such as dibutyl tin dilaurate. The mixture is then maintained at a temperature between 70° C. and 110° C. and preferably between 80° C. and 100° C. until the reaction is complete.

The preferred linear polyether polyurethanes are made from random polyoxyethylene-polyoxypropylene diol copolymers and a di-isocyanate with a ratio of isocyanate groups (NCO) to hydroxyl groups (OH) of between 0.3 to 0.9 and more preferably 0.5 to 0.7. Such preferred polyurethanes will absorb at least 10% water.

The visosity (as measured at 39° C. using a Ferranti-Shirley Cone and Plate Viscometer with a 1 cm radius cone and a 1200 g spring) of the preferred linear polyether polyurethane will suitably be between 500 and 10,000 Poise and preferably be between 1,500 and 6,000 Poise, for example 3,000 Poise.

The hydrophilic mobile gel and film forming the walls of the envelope and the adhesive when present are suitably transparent so that the condition of the skin beneath the device may be monitored during the wearing period.

The hydrophilic mobile gel may incorporate a substance, for example a cobalt salt, which will indicate by virtue of a colour change when the percentage of water absorbed into the gel has reached a certain level e.g. 50% indicating that the device should be replaced.

The hydrophilic mobile gel may incorporate less dense materials, for example glass or polystyrene microspheres so that a prophylactic device, when made from the hydrophilic mobile gel incorporating these less dense materials, will be lighter than an equivalent device made from the hydrophilic mobile gel alone.

The envelope may be formed by conventional means from the appropriate polymer film. Suitably the film may be formed into strips of the appropriate size, folded and heat sealed along two sides to provide an envelope with an opening or the envelopes may be blow moulded or vacuum formed from suitable polymer.

The size and shape of the device will vary depending upon the area of the body to which the device is to be applied.

By pressure bearing surface is meant those surfaces upon which the weight of a patient rests when, for example, in a prone position where the pressure bearing surfaces are for example the heels, sacrum and shoulder blades.

Certain apt devices of the invention contain at least two compartments. The first compartment is adapted to be placed beneath the pressure bearing surfaces of a prone or sitting patient. Such compartments are generally rectangular or square. The other compartments are present to give support to the body adjacent to the pressure bearing surfaces. With the heel this surface is the arch between the heel and the calf; with the sacrum it is the arch of the back. These compartments may be filled with gel so that they may be firmer than those supporting a pressure bearing surface. These compartments are shaped to take account of the contours. These compartments may provide support rather than disperse pressure but they should not be so firm as to create new pressure sores.

Suitably the envelope comprises two sealed compartments. Preferably the compartments are not in fluid communication with each other so that when the heel or sacrum is placed on the appropriate compartment the pressure is dissipated over that compartment only.

The heel or sacrum pressure bearing compartments will vary in size depending upon the area with which they are in contact but aptly in shape they will be in the form of a rectangle including a square. For use on the heel the pressure bearing compartment will suitably be in the form of a square the side of which is from 40 to 75 mm and preferably 55 to 60 mm long and is from 5 to 25 mm and preferably 10 to 15 mm in thickness and containing from 8 to 50 ml, preferably 20 to 30 ml of hydrophilic gel material.

For use on the sacrum the pressure bearing compartment will be suitably in the form of a rectangle which has a short side of from 40 to 60 mm in length, preferably 45 to 55 mm and a long side of from 80 to 120 mm, preferably 90 to 105 mm in length and from 5 to 25 mm and preferably 10 to 15 mm in thickness. Such compartments will contain from 20 to 150 ml of hydrophilic gel and preferably 25 to 50 ml of hydrophilic gel.

The second sealed compartment is shaped to provide support to the non pressure bearing surfaces adjacent to the heel or sacrum. Adjacent to the heel the shape of the compartment is such that it extends along the back of the leg to the calf. The shape of this compartment is that of a triangle which tapers from the heel along the leg and is also thicker adjacent to the heel and reduces in thickness along the leg. The triangular compartment is suitably 40 to 75 mm across its base and has a height of from 150 to 200 mm from base to the tip. The thickness of the compartment is suitably 18 to 25 mm adjacent to the heel and 5 to 15 mm thick at the pointed end. This compartment will contain more hydrophilic gel than the first compartment and will suitably contain 50 to 200 ml.

For use on the sacrum the second sealed compartment will extend to provide support for the back adjacent to the sacrum. The most suitable shape is that of a trapezium in which the narrower side is adjacent to the sacrum and the sides diverge. Suitably the compartment has a width of 80 to 120 mm which widens to 200 to 250 mm at the other edge. The length of the compartment is from 120 to 150 mm. Aptly when not stressed this compartment is flat and is from 10 to 20 mm thick. Aptly the second compartment will contain from 300 to 400 ml.

Preferred embodiments of the devices of the present invention will now be described by way of example only and with reference to the accompanying drawings in which.

Figure 1:
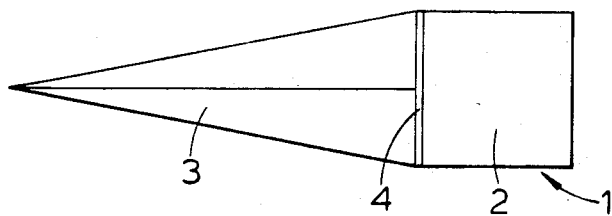
FIG. 1 shows a top view of a device suitable for application to the heel of a bedridden patient.

FIG. 1 shows a two-compartment device (1) which is suitable for use on the heel of a bedridden patient. The first compartment (2) is approximately square in shape and is filled with a mobile hydrophilic polyurethane gel to a thickness of about 10 mm, the dimension of the compartment being approximately 55 mm square. At this thickness the compartment provides a suitable pad for the heel. The second compartment (3) is triangular in shape tapering to approximately a point away from the heel. This compartment lies along the leg from the heel to the calf. This compartment is filled with a mobile hydrophilic polyurethane gel so that it is firmer to the touch than the first compartment. Suitably the thickness of this compartment is 20 mm narrowing to 12 mm at the pointed end. The walls of both compartments are formed from a moisture vapour permeable polyether polyamide block copolymer which is approximately 75 microns thick and is heat sealed around its edges to form the compartments. The two compartments are not in communication being separated by a seal line (4).

Figure 2:
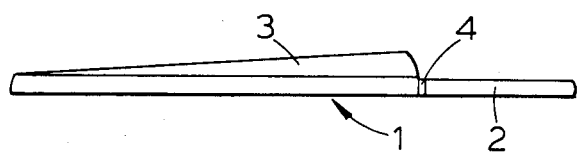
FIG. 2 shows a side view of the device shown in FIG. 1.

FIG. 2 shows a side view of the device shown in FIG. 1. This shows the difference in thickness of the two compartments. The second compartment (3) also has a variable thickness from the portion adjacent to the heel compartment to the point of the triangle. The thicker portion being adjacent to the heel so that the device follows the contours of the back of the leg. The envelope for this compartment is conveniently formed in this three dimensional form by vacuum moulding.

Figure 3:
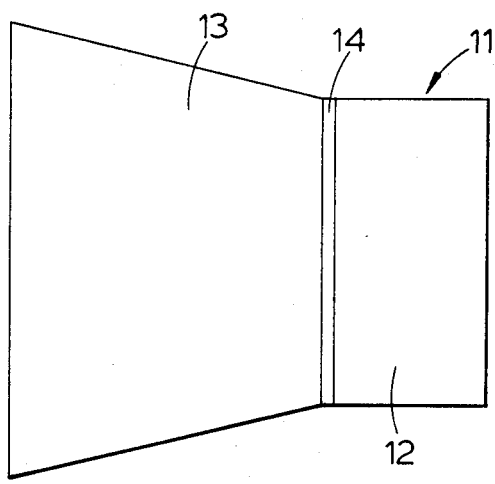
FIG. 3 shows a top view of a device suitable for application to the sacrum of a bedridden patient.

FIG. 3 shows a two compartment device (11) which is suitable for use on the sacrum of a bedridden patient. The first compartment (12) is rectangular in shape and is filed with a hydrophilic polyurethane gel to a thickness of 10 mm. The dimensions for the compartment are typically 100 mm by 55 mm. At this thickness the compartment provides a suitable pad for placing beneath the sacrum. The second compartment (13) is trapezoidal in shape with the narrower side of the trapezium adjaent to the sacrum bearing compartment. The compartment is filled with a hydrophilic polyurethane gel so that it may be firmer to the touch than is the first compartment. Suitably the thickness of this compartment is 15 mm. The walls of both containers are a moisture vapopur permeable polyether polyamide block copolymer which is approximately 75 microns thick and is heat sealed around the edge. The two compartments are not in communication being separated by a seal line (14).

Figure 4:
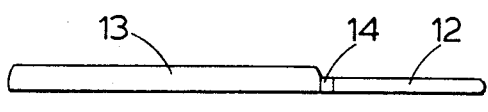
FIG. 4 shows a side view of the device shown in FIG. 3.

FIG. 4 shows a side view of the device shown in FIG. 3. The difference in thickness of the two compartments is clearly shown. In use on the sacrum and back the variation in thickness of the second compartment is not as critical as with the device for the heel.

Figure 5:
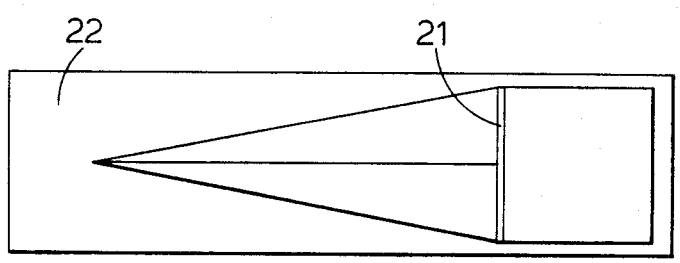
FIG. 5 shows a top view of a device for application to the heel which has around it an adhesive film margin.

FIG. 5 shows a two compartment device (21) which is suitable for use on the heel which is similar to the device of FIG. 1 except that a film carrying an adhesive is present as an adhesive margin (22) whereby the device may be adhered to the leg. Typically both the film and adhesive are moisture vapour permeable so that the device may be left on the skin for a long period without causing maceration to the underlying skin.

It follows from the foregoing descriptions of the shape of the devices and as exemplified in FIGS. 1 to 5 that a preferred embodiment of the present invention is a device in which one of the envelopes of the device narrows from an end to the opposed end so that one end of the envelope is wider than the other end.

EXAMPLE 1

Preparation of a device suitable for use on the sacrum

A linear polyurethane gel was prepared from the following:

| | |
|---|---|
| Polyethylene glycol (mol. wt. 600) | 219.0 g |
| Polypropylene glycol (mol. wt. 1025) | 1166.6 g |
| Ethanediol | 23.25 g |
| 4,4'1Dicyclohexylmethane di-isocyanate | 406.95 g |
| Di-n-butyl tin laurate (catalyst) | 0.28 g |

The first three ingredients were mixed together to form a homogenous mixture whilst warming to 60° C. The catalyst was then added. Finally the di-isocyanate was added with stirring. The resultant homogenous reaction mixture was poured into a mould and cured in an oven at 90° C. for 2 hours. The resultant hydrophilic polyurethane was obtained as a viscous, transparent, mobile gel.

A polyurethane film was cast onto a silicone release paper at a weight of 60 gsm using a polyurethane syrup comprising 100 parts of Estane 5714F (available from B. F. Goodrich Ltd.), 5 parts of Gasil 23 fine silica (available from Crossfield Chemical Ltd), 240 parts of tetrahydrofuran and 160 parts acetone. The resultant film was cut into strips so that on folding each strip in half and heat sealing the two edges, an envelope approximately 10 cm by 10 cm was formed.

A part of the anhydrous polyurethane gel prepared above (120 ml) was transferred to the polyurethane envelope and the envelope closed by heat sealing along the fourth edge.

The resultant pad 10 cm by 10 cm and 1.2 cm thick was suitable for use to prevent formation of pressure sores on the sacrum.

EXAMPLE 2

Preparation of a device for use on the sacrum

A linear polyurethane gel was prepared from the following:

| | |
|---|---|
| Random polyoxyethylene polyoxypropylene diol copolymer (Breox 75W270) (Mol. Wt. 2600) | 2,600 g |
| Water | 13.9 g |
| Irganox 1010 | 29.28 g |
| 4,4'-Dicyclohexylmethane di-isocyanate | 314 g |
| Di-n-butyl tin laurate (catalyst) | 0.585 g |

The first four ingredients were mixed together to form a homogenous mixture whilst warming to 60° C. The catalyst was then added with stirring. The resultant homogenous reaction mixture was poured into a mould and cured in an oven at 90° C. for 2 hours. The resultant hydrophilic polyurethane was obtained as a viscous, transparent mobile gel.

A polyether polyamide copolymer film was extruded in a conventional manner using a melt temperature of approximately 185° C. The resultant film thickness was approximately 170 microns. This film was moulded into the appropriate shape of approximately 10 cm×10 cm×3 cm deep using a vacuum mould. The average thickness of the film after vacuum moulding was approximately 75 microns.

A part of the anhydrous linear polyurethane gel prepared above (120 mls) was transferred to the pouch of polyether polyamide copolymer film formed in the vacuum mould. A further piece of extruded polyether polyamide copolymer film with a thickness of 75 microns was then heat sealed to the hydrophilic gel filled pouch in such a manner as to exclude all the air from the envelope thus formed. The polyether polyamide copolymer film thus sealed to the hydrophilic gel filled pouch extended on all sides by 10 cm beyond the hydrophilic gel filled envelope. This extended area of polyether polyamide film was coated with suitable pressure sensitive adhesive at a mass weight of 30 gsm. The adhesive face of the device was then placed onto a silicone release paper and the whole device sealed into a substantially vapour impermeable bag for storage.

EXAMPLE 3

Preparation of a device suitable for use on the sacrum

A linear polyurethane gel was prepared from the following:

| | |
|---|---|
| Random polyoxyethylene polyoxypropylyene diol copolymer (Breox 75W270) (Mol. Wt. 2600) | 2,600 g |
| Polypropylene glycol (Mol. Wt. 1,025) | 1,025 g |
| Irganox 1010 | 39.4 g |
| 4,4′Dicyclohexylmethane di-isocyanate | 314 g |
| Di-n-butyl tin laurate (catalyst) | 0.8 g |

The first four ingredients were mixed together to form a homogenous mixture whilst warming to 60° C. The catalyst was then added with stirring. The resultant homogenous reaction mixture was poured into a mould and cured in an oven at 90° C. for 2 hours. The resultant hydrophilic polyurethane was obtained as a viscous, transparent mobile gel.

A polyetherester block copolymer film was extruded in the conventional manner using a melt temperature of approximately 185°. The resultant film thickness was approximately 170 microns. This film was moulded into the appropriate shape of approximately 10 cm×10 cm×3 cm deep using a vacuum mould. The average thickness of the film after vacuum moulding was approximately 75 microns.

A part of the anhydrous linear polyurethane gel prepared above (120 mls) was transferred to the pouch of polyetherester block copolymer film formed in the vacuum mould. A further piece of extruded polyetherester block copolymer film with a thickness of 75 microns was then heat sealed to the hydrophilic gel filled pouch in such a manner as to exclude all the air from the envelope thus formed. The polyetherester block copolymer film thus sealed to the hydrophilic gel filled pouch extended on all sides 10 cm beyond the hydrophilic gel filled envelope. This extended area of polyetherester block copolymer film was coated with a suitable pressure sensitive adhesive at a mass weight of 30 gsm. The adhesive face of the device was then placed onto a silicone release paper and the whole device sealed into a substantially water vapour impermeable bag for storage.

EXAMPLE 4

Preparation of a device suitable for use on the heel

A linear polyurethane gel was prepared in the same manner as Example 2.

A polyether polyamide copolymer film was extruded in the conventional manner using a melt temperature of approximately 185° C. The resultant film thickness was approximately 170 microns. This film was moulded into the appropriate shape using a vacuum mould. The appropriate shape for a device for the heel is that shown and described in FIGS. 1 and 2 of this specification. The average thickness of the film after vacuum moulding was approximately 75 microns.

A part of the anhydrous linear polyurethane gel prepared above (100 ml) was transferred to the larger of the two pouches of the polyether polyamide copolymer film and 25 ml of the anhydrous linear polyurethane gel prepared above was transferred to the smaller of the two pouches of the polyether polyamide copolymer film formed in the vacuum mould. A further piece of extruded polyether polyamide copolymer film with a thickness of 75 microns was then heat sealed to the hydrophilic gel filled pouches in such a manner as to exclude all the air from the two independent envelopes thus formed. The polyether polyamide copolymer film thus sealed to the hydrophilic gel filled pouches extended on all sides by 10 cm beyond the hydrophilic gel filled envelopes. This extended area of polyether polyamide film was coated with a suitable pressure sensitive adhesive at a mass weight of 30 gsm. The adhesive face of the device was then placed onto a silicone release paper and the whole device sealed into a substantially water vapour impermeable bag for storage.

EXAMPLE 5

Preparation of a device suitable for use on the sacrum

A linear polyurethane gel was prepared as in Example 3.

A polyetherester block copolymer film was extruded in the conventional manner using a melt temperature of approximately 185° C. The resultant film thickness was approximately 170 microns. This film was then moulded into the appropriate shape using a vacuum mould. The appropriate shape for a device for the heel is that shown and described in FIGS. 1 and 2 of this specification. The average thickness of the film after vacuum moulding was approximately 75 microns.

A part of the anhydrous linear polyurethane gel prepared above (100 ml) was transferred to the larger of the two pouches of the polyetherester block copolymer film and 25 ml of the anhydrous linear polyurethane gel prepared above was transferred to the smaller of the two pouches of the polyetherester block copolymer film formed in the vacuum mould. A further piece of extruded polyetherester block copolymer film with a thickness of 75 microns was then heat sealed to the hydrophilic gel filled pouches in such a manner as to exclude all the air from the two independent envelopes thus formed. The polyetherester block copolymer film thus sealed to the hydrophilic gel filled pouches extended on all sides by 10 cm beyond the hydrophilic gel filled envelopes. This extended area of polyetherester block copolymer film was coated with a suitable pressure sensitive adhesive at a mass weight of 30 gsm. The adhesive face of the devices was then placed onto a silicone release paper and the whole device sealed into a substantially water vapour impermeable bag for storage.

Devices as described in Examples 2, 3, 4 and 5 have been tested and found to reduce the peak pressures, measured underneath a supine patient's heels from about 200 mmHg to about 40 mmHg, a reduction of approximately 80%.

I claim:

1. A device useful for the prophylaxis of pressure sores and which is removably attachable to the human body which device comprises a mobile moisture absorbing hydrophilic gel retained within a flexible elastomeric envelope which envelope has a body contacting surface which is a film having a moisture vapour transmission rate of greater than 300 g/m$^2$ 24 hr$^{-1}$ at 37° C. at 100% to 10% relative humidity difference said device being 5 to 25 mm thick.

2. A device according to claim 1 in which the body contacting surface film is coated with a pressure sensitive adhesive, the adhesive coated body contacting surface film having a moisture vapour transmission rate of greater than 500 g/m$^2$ 24 hr$^{-1}$ at 37° C. at 100% to 10% relative humidity difference.

3. A device according to claim 1 in which the film extends beyond the flexible elastomeric envelope to form a margin which is adhesive coated for attaching the device to the body.

4. A device according to claim 1 in which the mobile hydrophilic gel has a viscosity between 1500 and 6,000 Poise as measured at 39° C., using a 1 cm radius cone driven at 5 r.p.m., a 1200 g spring, using a Ferranti-Shirley Cone and Plate Viscometer.

5. A device according to claim 1 in which the mobile hydrophilic gel absorbs more than 10% water when in contact with water or moisture vapour.

6. A device according to claim 1 in which the device has a rate of water uptake greater than 150 mg/72 hrs/cm$^2$ of the skin contacting body surface of the gel filled envelope.

7. A device according to claim 1 in which the mobile hydrophilic gel is a hydrophilic polyurethane.

8. A device according to claim 7 in which the mobile hydrophilic gel is a linear hydrophilic polyurethane formed from a random polyoxyethylene polyoxypropylene diol copolymer and a di-isocyante such that the ratio of isocyanate groups to hydroxyl groups is between 0.5 and 0.7.

9. A device according to claim 1 in which the body contacting surface film is a polyurethane.

10. A device according to claim 1 in which the body contacting surface film is a polyetherester block copolymer or a polyether polyamide block copolymer.

11. A device according to claim 1 in which the device is sufficiently transparent to allow the appearance of the skin beneath the device to be viewed.

12. A device according to claim 1 in which the skin contact area of the envelope is less than 200 cm$^2$.

13. A device according to claim 1 in which the volume of hydrophilic mobile gel in the envelope is less than 300 cm$^3$.

14. A device according to claim 1 which comprises 1 to 10 envelopes.

* * * * *